US009480589B2

(12) United States Patent
Breyer et al.

(10) Patent No.: US 9,480,589 B2
(45) Date of Patent: Nov. 1, 2016

(54) ENDOPROSTHESIS DELIVERY SYSTEM (75) Inventors: Debbie Breyer, Waverly, MN (US); Michael Gerdts, Big Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2161 days.

(21) Appl. No.: 11/129,136

(22) Filed: May 13, 2005

(65) Prior Publication Data
US 2006/0259114 A1 Nov. 16, 2006

(51) Int. Cl.
| | | |
|---|---|---|
| A61F 2/06 | (2013.01) | |
| A61F 2/966 | (2013.01) | |
| A61F 2/95 | (2013.01) | |
| A61F 2/958 | (2013.01) | |

(52) U.S. Cl.
CPC ............... *A61F 2/966* (2013.01); *A61F 2/95* (2013.01); *A61F 2002/9583* (2013.01); *A61F 2250/0036* (2013.01); *A61F 2250/0039* (2013.01)

(58) Field of Classification Search
CPC ............ A61M 25/0045; A61M 25/0053; A61M 25/0005; A61M 25/0012; A61M 25/0023; A61M 25/00; A61M 25/001; A61M 25/0013; A61M 2025/0024; A61M 25/0026; A61M 25/0028–25/003; A61M 2025/0034; A61M 2025/0035–2025/004; A61M 2025/0046–2025/0048; A61M 25/005; A61M 25/0051–25/0054; A61M 25/0067; A61M 25/0068; A61M 25/0074; A61M 25/008; A61M 25/01; A61M 25/0141; A61M 25/0144; A61F 2/95; A61F 2/966; A61F 2/962; A61F 2002/9522; A61F 2002/9528; A61F 2002/9534; A61F 2/954; A61F 2/958; A61F 2002/9665; A61F 2/97; A61F 2/02; A61F 2/04; A61F 2002/011; A61F 2250/0009; A61F 2250/00; A61F 2250/0018–2250/0019; A61F 2250/0036; A61B 2017/320056
USPC ................ 623/1.11, 1.23; 606/108; 604/525
See application file for complete search history.

(56) References Cited

U.S. PATENT DOCUMENTS

| | | | |
|---|---|---|---|
| 4,846,812 A | | 7/1989 | Walker et al. |
| 4,960,410 A | | 10/1990 | Pinchuk |
| 5,156,594 A | * | 10/1992 | Keith ..................... 604/103.09 |
| 5,209,729 A | * | 5/1993 | Hofmann et al. ........ 604/102.02 |
| 5,254,107 A | | 10/1993 | Soltesz |
| 5,387,235 A | * | 2/1995 | Chuter ........................ 623/1.11 |
| 5,470,322 A | | 11/1995 | Horzewski et al. |
| 5,484,444 A | * | 1/1996 | Braunschweiler et al. . 623/1.11 |
| 5,496,294 A | * | 3/1996 | Hergenrother .... A61M 25/0052 604/264 |
| 5,531,719 A | * | 7/1996 | Takahashi ...................... 604/525 |

(Continued)

FOREIGN PATENT DOCUMENTS

| | | | | |
|---|---|---|---|---|
| EP | 0696447 | | 1/2000 | |
| EP | 1025813 A2 | * | 8/2000 | ............... A61F 2/06 |

(Continued)

OTHER PUBLICATIONS

Schetsky, L. McDonald, "Shape Memory Alloys," Encyclopedia of Chemical Technology (3$^{rd}$. Ed.), John Wiley & Sons, 1982, vol. 20, pp. 726-736.

(Continued)

*Primary Examiner* — Melanie Tyson
*Assistant Examiner* — Erin Colello
(74) *Attorney, Agent, or Firm* — Seager, Tufte & Wickhem, LLP (57) ABSTRACT

Implantable medical endoprosthesis delivery systems as well as related systems and methods are disclosed.

21 Claims, 4 Drawing Sheets

(56) References Cited

U.S. PATENT DOCUMENTS

| | | | |
|---|---|---|---|
| 5,533,985 A * | 7/1996 | Wang | 604/264 |
| 5,534,007 A * | 7/1996 | St. Germain et al. | 623/1.11 |
| 5,542,937 A * | 8/1996 | Chee et al. | 604/523 |
| 5,545,209 A * | 8/1996 | Roberts et al. | 623/1.11 |
| 5,554,139 A * | 9/1996 | Okajima | 604/526 |
| 5,603,698 A * | 2/1997 | Roberts et al. | 604/104 |
| 5,622,665 A | 4/1997 | Wang | |
| 5,639,274 A | 6/1997 | Fischell et al. | |
| 5,676,659 A | 10/1997 | McGurk | |
| 5,690,644 A * | 11/1997 | Yurek et al. | 623/1.11 |
| 5,702,373 A * | 12/1997 | Samson | A61M 25/005 604/526 |
| 5,755,704 A * | 5/1998 | Lunn | 604/527 |
| 5,772,669 A | 6/1998 | Vrba | |
| 5,792,124 A * | 8/1998 | Horrigan | A61M 25/001 604/265 |
| 5,800,391 A * | 9/1998 | Kontos | 604/96.01 |
| 5,833,694 A | 11/1998 | Poncet | |
| 5,851,203 A | 12/1998 | van Muiden | |
| 5,860,963 A * | 1/1999 | Azam | A61L 2/08 138/124 |
| 5,876,374 A * | 3/1999 | Alba et al. | 604/164.08 |
| 5,893,868 A | 4/1999 | Hanson et al. | |
| 5,918,643 A * | 7/1999 | Roloff | F16L 11/045 138/137 |
| 5,951,585 A * | 9/1999 | Cathcart et al. | 606/198 |
| 5,961,536 A * | 10/1999 | Mickley et al. | 606/194 |
| 6,019,778 A * | 2/2000 | Wilson et al. | 606/198 |
| 6,022,341 A | 2/2000 | Lentz | |
| 6,030,369 A * | 2/2000 | Engelson et al. | 604/264 |
| 6,045,547 A | 4/2000 | Ren et al. | |
| 6,045,734 A | 4/2000 | Luther et al. | |
| 6,053,904 A * | 4/2000 | Scribner et al. | 604/527 |
| 6,059,769 A | 5/2000 | Lunn et al. | |
| 6,059,813 A * | 5/2000 | Vrba et al. | 606/198 |
| 6,077,295 A | 6/2000 | Limon et al. | |
| 6,077,297 A * | 6/2000 | Robinson et al. | 623/1.11 |
| 6,106,510 A | 8/2000 | Lunn et al. | |
| 6,113,579 A * | 9/2000 | Eidenschink et al. | 604/264 |
| 6,126,685 A * | 10/2000 | Lenker et al. | 623/1.11 |
| 6,129,708 A * | 10/2000 | Enger | 604/103.04 |
| 6,135,992 A | 10/2000 | Wang | |
| 6,159,228 A | 12/2000 | Frid et al. | |
| 6,171,327 B1 * | 1/2001 | Daniel | A61F 2/01 606/159 |
| 6,217,565 B1 * | 4/2001 | Cohen | 604/525 |
| 6,240,231 B1 * | 5/2001 | Ferrera et al. | 385/115 |
| 6,328,731 B1 | 12/2001 | Ouchi | |
| 6,350,278 B1 * | 2/2002 | Lenker et al. | 623/1.12 |
| 6,368,344 B1 | 4/2002 | Fitz | |
| 6,379,365 B1 * | 4/2002 | Diaz | 606/108 |
| 6,380,457 B1 * | 4/2002 | Yurek et al. | 623/1.11 |
| 6,425,898 B1 * | 7/2002 | Wilson et al. | 606/108 |
| 6,491,619 B1 * | 12/2002 | Trauthen et al. | 600/3 |
| 6,520,983 B1 * | 2/2003 | Colgan et al. | 623/1.11 |
| 6,562,021 B1 | 5/2003 | Derbin et al. | |
| 6,663,614 B1 * | 12/2003 | Carter | 604/525 |
| 6,663,651 B2 * | 12/2003 | Krolik | A61F 2/013 128/899 |
| 6,689,120 B1 * | 2/2004 | Gerdts | 604/526 |
| 6,702,802 B1 * | 3/2004 | Hancock | A61F 2/958 604/104 |
| 6,702,843 B1 * | 3/2004 | Brown et al. | 623/1.11 |
| 6,726,712 B1 * | 4/2004 | Raeder-Devens et al. | 623/1.11 |
| 6,755,855 B2 * | 6/2004 | Yurek et al. | 623/1.12 |
| 6,858,024 B1 * | 2/2005 | Berg | A61M 25/0013 604/525 |
| 6,939,353 B2 * | 9/2005 | Que | A61B 17/221 604/264 |
| 6,942,688 B2 * | 9/2005 | Bartholf et al. | 623/1.11 |
| 7,137,993 B2 * | 11/2006 | Acosta et al. | 623/1.11 |
| 7,163,552 B2 * | 1/2007 | Diaz | 623/1.12 |
| 7,166,099 B2 * | 1/2007 | Devens, Jr. | A61M 25/0045 604/523 |
| 7,166,100 B2 * | 1/2007 | Jordan | A61M 25/10 604/524 |
| 7,169,105 B2 * | 1/2007 | Iwasaka | A61B 1/00071 600/139 |
| 7,597,830 B2 * | 10/2009 | Zhou | A61M 25/001 264/138 |
| 7,887,574 B2 * | 2/2011 | McFerran | 623/1.11 |
| 2001/0034549 A1 * | 10/2001 | Bartholf et al. | 623/1.12 |
| 2001/0041881 A1 * | 11/2001 | Sarge et al. | 604/525 |
| 2002/0045929 A1 * | 4/2002 | Diaz | 623/1.11 |
| 2002/0052640 A1 * | 5/2002 | Bigus | A61F 2/07 623/1.11 |
| 2002/0156459 A1 * | 10/2002 | Ye et al. | 604/527 |
| 2002/0156460 A1 * | 10/2002 | Ye | A61L 29/085 604/534 |
| 2002/0161425 A1 * | 10/2002 | Hemerick | A61F 2/966 623/1.11 |
| 2003/0014062 A1 * | 1/2003 | Houser et al. | 606/153 |
| 2003/0050686 A1 * | 3/2003 | Raeder-Devens et al. | 623/1.11 |
| 2003/0083691 A1 | 5/2003 | Wantink | |
| 2003/0093059 A1 | 5/2003 | Griffin et al. | |
| 2003/0100849 A1 * | 5/2003 | Jang | 600/585 |
| 2003/0199836 A1 * | 10/2003 | Tiernan | A61M 25/0009 604/264 |
| 2003/0212429 A1 * | 11/2003 | Keegan | A61F 2/01 606/200 |
| 2004/0059404 A1 * | 3/2004 | Bjorklund | A61N 1/056 607/126 |
| 2004/0064130 A1 * | 4/2004 | Carter | A61M 25/0045 604/523 |
| 2004/0093011 A1 * | 5/2004 | Vrba | A61B 5/1076 606/200 |
| 2004/0093061 A1 * | 5/2004 | Acosta et al. | 623/1.11 |
| 2004/0210211 A1 | 10/2004 | Devens, Jr. et al. | |
| 2005/0060016 A1 * | 3/2005 | Wu et al. | 623/1.11 |
| 2005/0090890 A1 * | 4/2005 | Wu | A61F 2/95 623/1.11 |
| 2005/0149160 A1 * | 7/2005 | McFerran | 623/1.11 |
| 2005/0182475 A1 * | 8/2005 | Jen et al. | 623/1.11 |
| 2005/0251197 A1 * | 11/2005 | Hensley | A61F 2/01 606/200 |
| 2005/0267563 A1 * | 12/2005 | Case et al. | 623/1.11 |
| 2006/0030835 A1 * | 2/2006 | Sherman et al. | 604/526 |
| 2006/0074477 A1 | 4/2006 | Berthiaume et al. | |
| 2006/0229697 A1 * | 10/2006 | Gerdts | A61F 2/95 623/1.11 |
| 2006/0229698 A1 * | 10/2006 | Larson et al. | 623/1.11 |
| 2008/0294230 A1 * | 11/2008 | Parker | A61F 2/95 623/1.11 |

FOREIGN PATENT DOCUMENTS

| | | | |
|---|---|---|---|
| EP | 1053722 | 11/2000 | |
| EP | 1053722 A2 * | 11/2000 | A61F 2/06 |
| EP | 1025813 | 7/2006 | |
| WO | WO 02/056798 | 7/2002 | |

OTHER PUBLICATIONS

U.S. Appl. No. 11/093,448, filed Mar. 30, 2005, entitled "Catheter".

* cited by examiner

ENDOPROSTHESIS DELIVERY SYSTEM

TECHNICAL FIELD

This invention relates to systems for delivering medical devices, as well as related systems and methods.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include a sheath surrounding an inner member with a stent positioned therebetween. Generally, the operator of the system positions the distal portion within the lumen at a desired location (e.g., so that the stent is adjacent an occlusion). The operator can then retract the sheath to allow the stent to engage the occlusion/lumen wall. Thereafter, the operator removes the distal portion of the system from the lumen.

SUMMARY

In general, the invention relates to systems for delivering medical devices, as well as related methods. The systems can be used as, for example, implantable medical endoprosthesis delivery systems (e.g., stent delivery systems). The systems can be used, for example, to deploy a medical endoprosthesis (e.g., a stent) at a desired location within a lumen of a subject (e.g., an artery of a human).

The systems generally include an outer member having at least one layer and an inner member at least partially surrounded by the outer member. The outer and inner members are typically configured so that a medical endoprosthesis can be disposed between them.

In some embodiments, the at least one layer of the outer member is thicker at a first position proximal of its distal end than at a second position closer to the distal end than the first position.

In some embodiments, the outer member defines a first inner diameter and a first outer diameter at a first position proximal of its distal end and a second inner diameter and a second outer diameter at a second position closer to the distal end than the first position. In certain embodiments, a ratio of the difference between the second inner diameter and the first inner diameter to the difference between the second outer diameter and the first outer diameter is greater than 1.

The systems can enhance accurate deployment of an implantable endoprosthesis by reducing (e.g., preventing) elongation of the outer member and/or by reducing (e.g., preventing) shortening of the inner member during deployment of the endoprosthesis.

Other features and advantages of the invention will be apparent from the description, drawings and claims.

DESCRIPTION OF DRAWINGS

Like reference symbols in the various drawings indicate like elements.

DETAILED DESCRIPTION

Figure 1:
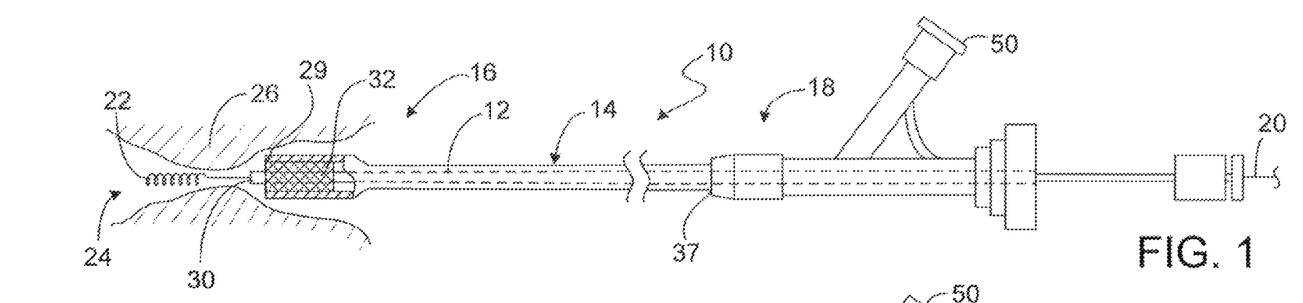
FIGS. 1-3 are side views of an embodiment of an endoprosthesis delivery system during use.
Figure 2:
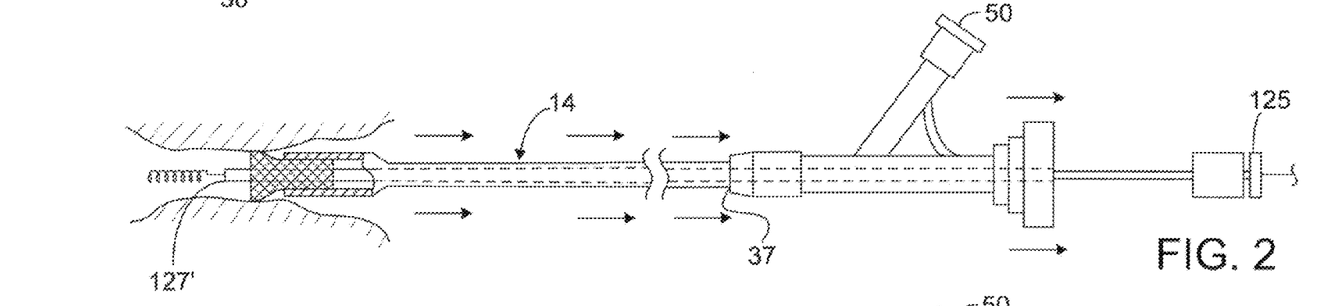
Figure 3:
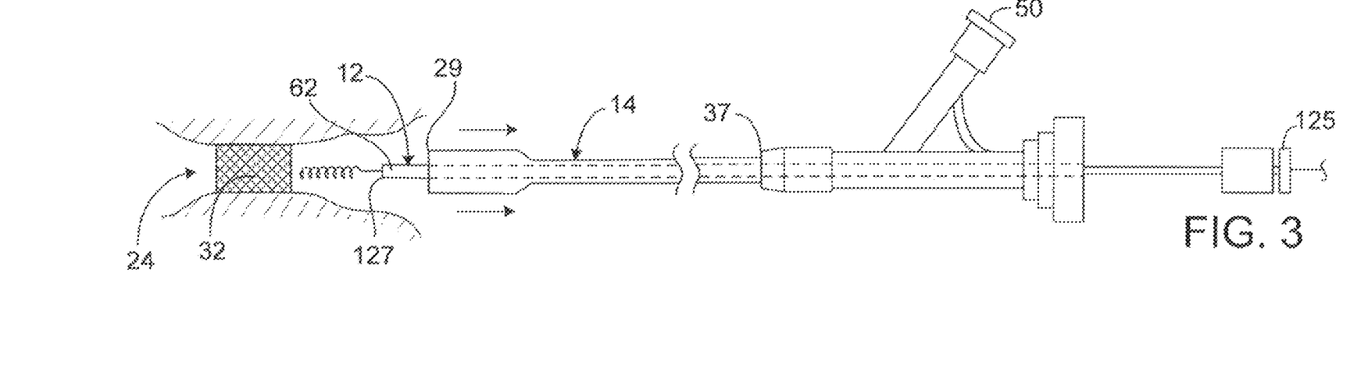

FIGS. 1-3 show an implantable medical endoprosthesis delivery system 10 that includes an inner member 12, an outer member 14 (e.g., a sheath) surrounding inner member 12, and a stent 32 positioned between inner member 12 and outer member 14. The delivery system 10 includes a distal end 16 dimensioned for insertion into a body lumen (e.g., an artery of a human) and a proximal end 18 that resides outside the body of a subject, and that contains at least one port 50 and lumens for manipulation by a physician. In an exemplary use of system 10, a guide wire 20 with a blunted end 22 is inserted into a body lumen 24 by making an incision in the femoral artery, and directing guide wire 20 to a constricted site 26 of lumen 24 (e.g., an artery constricted with plaque) using, for example, fluoroscopy as a position aid. After guide wire 20 has reached constricted site 26 of body lumen 24, inner member 12, stent 32 and outer member 14 are placed over the proximal end of guide wire 20. Inner member 12, stent 32 and outer member 14 are moved distally over guide wire 20 and positioned within lumen 24 so that stent 32 is adjacent constricted site 26 of lumen 24. A radiopaque marker band disposed about outer member 14 can assist device placement and deployment. Outer member 14 is moved proximally, allowing stent 32 to expand and engage constricted site 26. Outer member 14, inner member 12 and guide wire 20 are removed from body lumen 24, leaving stent 32 engaged with constricted site 26.

Figure 4A:
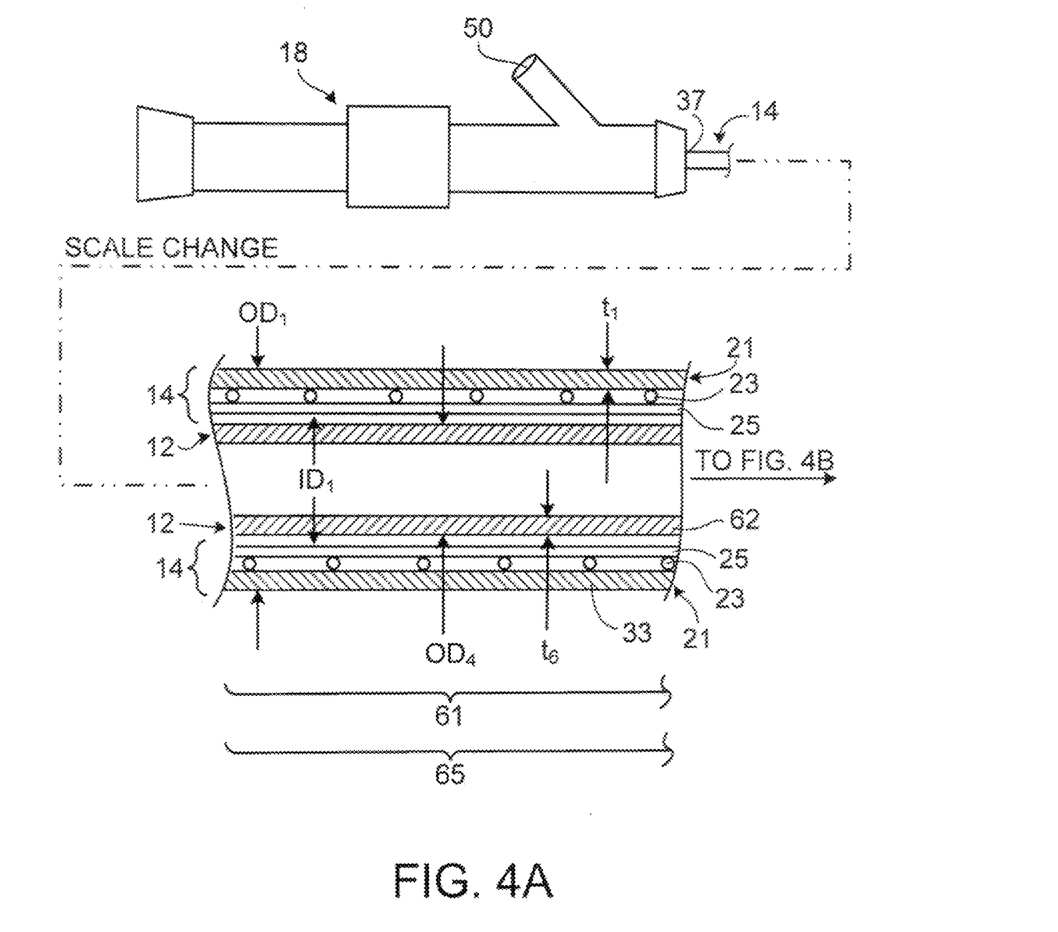
FIGS. 4a and 4b are exploded, mixed views of an embodiment of an endoprosthesis delivery system.
Figure 4B:
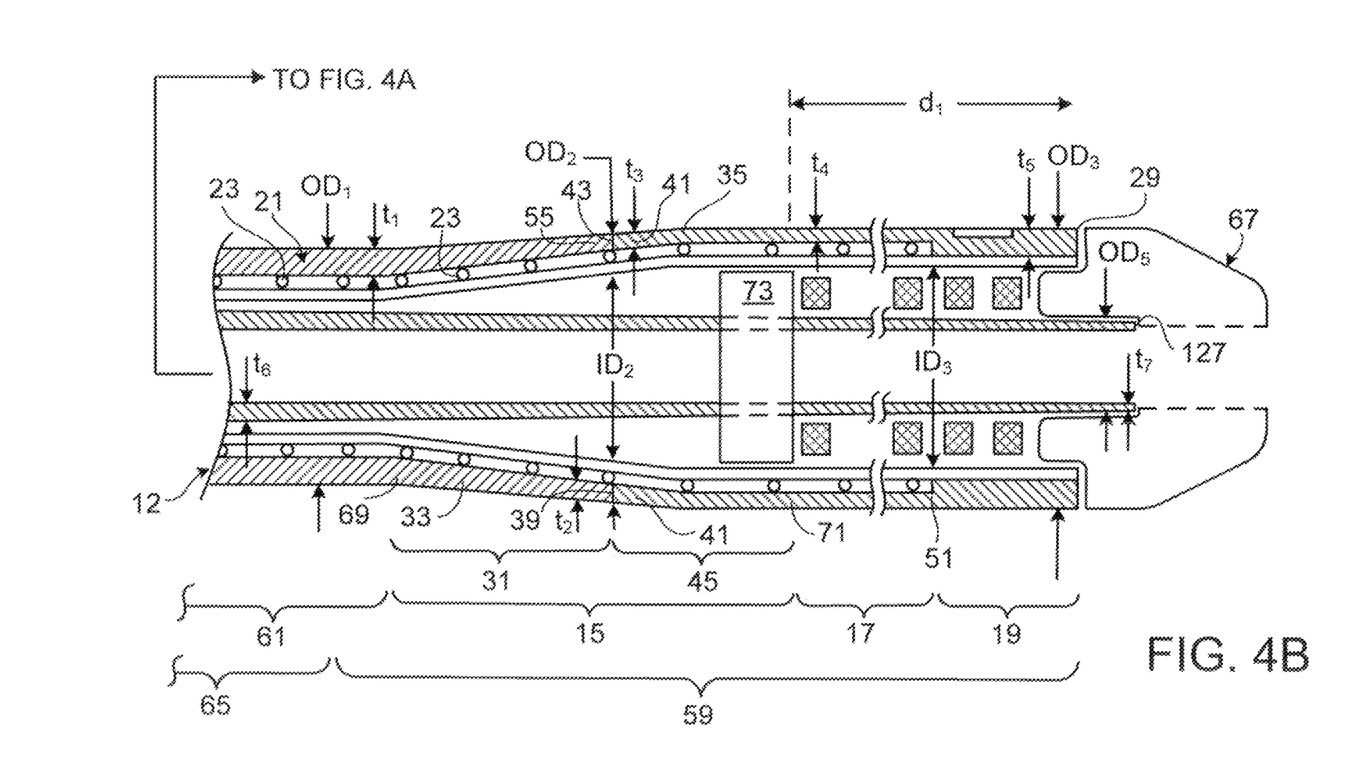

Referring to FIGS. 4a and 4b, outer member 14 extends between a proximal end 37 and a distal end 29. At least a portion of outer member 14 is multilayered, defining an outer layer 21, an intermediate layer 23, and an inner layer 25. Along its length, outer member 14 defines a proximal portion 61, a transition portion 15, a medial portion 17, and a distal portion 19.

The thickness of outer layer 21 varies along its length. Outer layer 21 defines a thickness t1 within proximal portion 61 of outer member 14. Outer layer 21 defines a thickness that decreases (e.g., continuously) from t1 to a thickness t4 within transition portion 15. Outer layer 21 defines a thickness t2 at a medial point 39 of transition portion 15. Outer layer 21 generally maintains thickness t4 within medial portion 17. Outer layer 21 defines a thickness t5 within distal portion 19.

In an exemplary embodiment, t1 is about 152 microns, t2 is about 115 microns, t4 is about 76 microns, and t5 is about 100 microns. In some embodiments, thickness t1 is at least about 125 microns (e.g., at least about 135 microns, at least about 140 microns, at least about 145 microns). In some embodiments, thickness t1 is no greater than about 225 microns (e.g., no greater than about 190 microns, no greater than about 180 microns, no greater than about 175 microns). In some embodiments, thickness t2 is at least about 80 microns (e.g., at least about 100 microns, at least about 115 microns, at least about 125 microns). In some embodiments, thickness t2 is no greater than about 135 microns (e.g., no greater than about 125 microns, no greater than about 115 microns, no greater than about 90 microns). In some embodiments, thickness t4 is at least about 50 microns (e.g., at least about 60 microns, at least about 70 microns, at least about 75 microns). In some embodiments, thickness t4 is no greater than about 110 microns (e.g., no greater than about 95 microns, no greater than about 90 microns, no greater than about 85 microns). In some embodiments, thickness t5 is at least about 80 microns (e.g., at least about 90 microns, at least about 100 microns). In some embodiments, thickness t5 is no greater than about 125 microns (e.g., no greater than about 115 microns, no greater than about 110 microns, no greater than about 105 microns). In some embodiments, t1 is at least about 10% (e.g., at least about 15%, at least about 20%) thicker than t2.

The inner diameter of outer member 14 varies along its length. Outer member 14 defines an inner diameter ID1 within proximal portion 61. Outer member 14 defines an inner diameter that increases (e.g., continuously) from ID1 to an inner diameter ID3 within transition portion 15. Outer member 14 defines an inner diameter ID2 at medial point 39 of transition portion 15. Outer member 14 generally maintains inner diameter ID3 within medial portion 17 and distal portion 19.

In some embodiments, ID1 is at least about 1.3 mm (e.g., at least about 1.4 mm, at least about 1.55 mm, at least about 1.65 mm). In some embodiments, ID1 is no greater than about 1.45 mm (e.g., no greater than about 1.57 mm, no greater than about 1.68 mm, no greater than about 1.93 mm). In some embodiments, ID2 is at least about 1.38 mm (e.g., at least about 1.5 mm, at least about 1.64 mm, at least about 1.76 mm). In some embodiments, ID2 is no greater than about 1.55 mm (e.g., no greater than about 1.68 mm, no greater than about 1.8 mm, no greater than about 2.05 mm). In some embodiments, ID3 is at least about 1.47 mm (e.g., at least about 1.6 mm, at least about 1.75 mm, at least about 1.88 mm). In some embodiments, ID3 is no greater than about 1.66 mm (e.g., no greater than about 1.8 mm, no greater than about 1.93 mm, no greater than about 2.2 mm). In an exemplary embodiment, ID1 is about 1.5 mm, ID2 is about 1.62 mm, and ID3 is about 1.78 mm.

The outer diameter of outer member 14 varies along its length. Outer member 14 defines an outer diameter OD1 within proximal portion 61. The outer diameter of outer member 14 increases continuously from OD1 to an outer diameter OD3 within transition portion 15. Outer member 14 defines an outer diameter OD2 at medial point 39 of transition portion 15. Outer member 14 generally maintains outer diameter OD3 within medial portion 17 and distal portion 19.

In some embodiments, OD1 is at least about 1.6 mm (e.g., at least about 1.75 mm, at least about 1.90 mm, at least about 2.05 mm). In some embodiments, OD1 is no greater than about 1.8 mm (e.g., no greater than about 1.95 mm, no greater than about 2.1 mm, no greater than about 2.4 mm). In some embodiments, OD2 is at least about 1.64 mm (e.g., at least about 1.8 mm, at least about 1.95 mm, at least about 2.1 mm). In some embodiments, OD2 is no greater than about 1.85 mm (e.g., no greater than about 2.0 mm, no greater than about 2.15 mm, no greater than about 2.45 mm). In some embodiments, OD3 is at least about 1.68 mm (e.g., at least about 1.84 mm, at least about 2.0 mm, at least about 2.15 mm). In some embodiments, OD3 is no greater than about 1.9 mm (e.g., no greater than about 2.05 mm, no greater than about 2.2 mm, no greater than about 2.5 mm). In an exemplary embodiment, OD1 is about 1.93 mm, OD2 is about 1.98 mm, and OD3 is about 2.03 mm.

Proximal portion 61 of outer member 14 extends between proximal end 37 of the outer member and a distal end 69 of the proximal portion. In some embodiments, proximal portion 61 is at least about 50% as long (e.g., at least about 65% as long, at least about 80% as long) as outer member 14. Without wishing to be bound by theory, it is believed that the relatively thicker outer layer 21 within proximal portion 61 as compared to the thinner outer layer 21 within medial portion 17 provides pushability when moving outer member 14 distally over guidewire 20 and resistance to elongation when moving outer member 14 proximally to deploy stent 32.

Transition portion 15 of outer member 14 extends between distal end 69 of proximal portion 61 and a distal end 71 of the transition portion. In some embodiments, the length of transition region 31 is at least about 5 mm (e.g., at least about 15 mm, at least about 25 mm, at least about 35 mm). In some embodiments, the length of transition region 31 is no more than about 10 mm (e.g., no more than about 20 mm, no more than about 30 mm, no more than about 45 mm).

Distal end 71 of transition portion 15 is proximal to at least a portion (e.g., most or all) of stent 32. In some embodiments, a longitudinal distance d1 between distal end 71 and distal end 29 of outer member 14 is at least about 70 mm (e.g., at least about 90 mm, at least about 115 mm, at least about 150 mm). In some embodiments, d1 is no greater than about 95 mm (e.g., no greater than about 120 mm, no greater than about 150 mm, no greater than about 225 mm). In an exemplary embodiment, d1 is about 120 mm.

Medial portion 17 of outer member 14 extends between distal end 71 of transition portion 15 and a distal end 51 of the medial portion. In some embodiments, the length of medial portion 17 is long enough to accommodate most (e.g., all) of stent 32 therein.

The relatively thinner outer layer 21 within medial portion 17 as compared to the thicker outer layer 21 within proximal portion 61 allows the medial portion to have a relatively larger inner diameter without a commensurately larger outer diameter as compared to the proximal portion. For example, in some embodiments, a ratio of a difference between ID3 and ID1 to a difference between OD3 and OD1 greater than 1 (e.g., at least about 2, at least about 2.75, at least about 3.25, at least about 4.5, at least about 6). The relatively larger inner diameter of medial portion 17 relative to proximal portion 61 allows stent 32 to be accommodated in the medial portion without damage. The relatively smaller change in the outer diameter of medial portion 17 relative to proximal portion 61 allows the distal end 16 of system 10 to be more easily manipulated within a body lumen.

Distal portion 19 of outer member 14 extends between distal end 51 of medial portion 17 and distal end 29 of outer member 14. As seen in FIG. 4b, intermediate layer 23 terminates at distal end 51 of the medial portion. Hence, distal portion 19 is bilayered defined by outer layer 21 and inner layer 25. As seen in FIG. 4b, distal end 29 of outer member 14 is disposed distal to at least about 50% (e.g., at least about 75% or all) of stent 32.

Outer layer 21 includes different, generally polymeric materials along its length. A proximal outer layer 33 formed of a first material extends between proximal end 37 of outer member 14 and a distal end 55 of the proximal outer layer. A distal outer layer 35 formed of a second different material extends between a proximal end 41 of the distal outer layer and distal end 29 of outer member 14.

The first material from which proximal outer layer 33 is formed has a higher durometer than the second material from which distal outer layer 35 is formed. In some embodiments, the first material is a polymeric material having a durometer of at least about 72 D (e.g., at least about 75 D, at least about 77 D, at least about 79 D). In some embodiments, the first material is a polymeric material having a durometer of no more than about 90 D. In some embodiments, the second material is a polymeric material having a durometer of no more than about 68 D (e.g., no more than about 70 D, no more than about 72 D). In an exemplary embodiment, proximal outer layer 33 is formed of a polyamide (e.g., a nylon, such as Vestamid 2101) having a durometer of between about 75 D and 80 D and distal outer layer 35 is formed of a polyether amide (e.g., a PEBAX) having a durometer of about 70 D. Without wishing to be bound by theory, it is believed that the higher durometer first material of the proximal portion reduces elongation of outer member 14 when it is moved proximally to deploy stent 32.

Proximal outer layer 33 and distal outer layer 35 are joined at a junction 43, which is disposed proximal to at least a portion (e.g., most or all) of stent 32. Junction 43 is a butt joint at which distal end 55 of proximal outer layer 33 abuts proximal end 41 of distal outer layer 35 without overlapping. Other types of junctions (e.g. lap joints) can be used.

Proximal outer layer 33 defines a transition region 31 in which the thickness of outer layer 21 decreases (e.g., continuously) from t1 to t2. In some embodiments, the length of transition region 31 is at least about 5 mm (e.g., at least about 10 mm, at least about 20 mm, at least about 30 mm). In some embodiments, the length of transition region 31 is no more than about 7.5 mm (e.g., no more than about 15 mm, no more than about 25 mm, no more than about 35 mm).

At junction 43, proximal end 41 of distal outer layer 35 defines a thickness t3 that is about the same as or somewhat less than thickness t2 of distal end 39 of proximal outer layer 33. In an exemplary embodiment, t2 and t3 are each about 115 microns.

Distal outer layer 35 defines a transition region 45 in which the thickness decreases (e.g., continuously) from a thickness t3 to t4. In some embodiments, the length of transition region 45 is at least about 5 mm (e.g., at least about 10 mm, at least about 20 mm, at least about 30 mm). In some embodiments, the length of transition region 31 is no more than about 7.5 mm (e.g., no more than about 15 mm, no more than about 25 mm, no more than about 35 mm).

Turning now to other components of outer member 14, inner layer 25 extends between proximal and distal ends 37, 29 of outer member 14. Inner layer 25 has a generally uniform thickness along its length. In some embodiments, inner layer 25 is at least about 13 microns thick (e.g., at least about 19 microns thick). In some embodiments, layer 25 is no greater than about 25 microns thick (e.g., no greater than about 30 microns thick). In general, layer 25 is formed from a lubricious material such as PTFE.

Intermediate layer 23 is disposed between outer layer 21 and inner layer 25. Intermediate layer 23 extends from proximal end 37 of outer member 14 to a distal end 51 of the intermediate layer. Distal end 51 of intermediate layer 23 is disposed proximal of distal end 29 of other outer member 14. In some embodiments, distal end 51 is disposed at least about 1 mm from distal end 29 (e.g., at least about 2 mm, at least about 3 mm). In some embodiments, distal end 51 is disposed no more than about 1.5 mm (e.g., no more than about 2.5 mm, no more than about 3.5 mm) from distal end 29.

As seen in FIG. 4b, intermediate layer is a braid (e.g., a weave or mesh) defined by a plurality of strands. In some embodiments, the strands of the braid are ribbons (e.g., flat) having a width of between about 63 microns and about 90 microns (e.g., a width of about 75 microns) and a thickness of between about 12 microns and about 25 microns (e.g., a thickness of about 17.5 microns). Typically, the pic count of the braid is between about 2.7 and about 3.5 pics mm$^{-1}$. In general, the geometry of the braid is a paired over-under geometry with pairs of adjacent strands passing over and then under (e.g., woven over and under) successive adjacent pairs of strands.

Outer member 14 can be formed as desired. In some embodiments, outer member 14 is formed using a tapered mandrel having an outer diameter generally complementary to the inner diameter of the outer member. For example, the method typically includes drawing inner layer 25 over the tapered mandrel (e.g., by sliding a tube of the inner layer material over the mandrel or coating the tapered mandrel with the inner layer material). Intermediate layer 23 is positioned (e.g., drawn over or braided over) the inner layer. The proximal outer layer and distal outer layer are drawn over the intermediate layer so that the distal end 39 of the proximal outer layer abuts the proximal end 41 of the distal outer layer. A layer of heat shrink material is placed over the proximal and distal outer layers. The layers are heated to a temperature sufficient to flow the proximal and distal outer layers about the intermediate layer 23.

Turning now to inner member 12 of system 10, the inner member includes a tube 62, which extends between a proximal end 125 and a distal end 127 (FIGS. 2 and 3). Returning to FIGS. 4a and 4b, a thickness of tube 62 varies along its length. Tube 62 defines a thickness t6 within a proximal portion 65 and a smaller thickness t7 at distal end 127. The thickness of tube 62 decreases (e.g., continuously) from t6 to t7 within a transition portion 59, which extends from proximal portion 65 to distal end 127.

In some embodiments, thickness t6 is at least about 185 microns (e.g., at least about 195 microns, at least about 205 microns, at least about 220 microns). In some embodiments, thickness t6 is no greater than about 240 microns (e.g., no greater than about 215 microns, no greater than about 210 microns, no greater than about 200 microns). In some embodiments, thickness t7 is at least about 85 microns (e.g., at least about 100 microns, at least about 105 microns, at least about 110 microns). In some embodiments, thickness t7 is no greater than about 130 microns (e.g., no greater than about 115 microns, no greater than about 110 microns, no greater than about 100 microns). In an exemplary embodiment, thickness t6 is about 210 microns and thickness t7 is about 105 microns.

The outer diameter of tube 62 varies along its length. Tube 62 defines an outer diameter OD4 within proximal portion 65 and an outer diameter OD5 at its distal end 127. OD5 is less than OD4. The outer diameter of tube 62 decreases (e.g., continuously) from OD4 to OD5 within transition portion 59. In some embodiments, at least a portion of transition portion 59 of inner member 12 is aligned with (e.g., surrounded by) at least a portion of transition portion 15 of outer member 14.

In some embodiments, OD4 of medial portion 65 is at least about 1.2 mm (e.g., at least about 1.3 mm, at least about 1.4 mm, at least about 1.5 mm). In some embodiments, OD4 is no greater than about 1.35 mm (e.g., no greater than about 1.45 mm, no greater than about 1.55 mm, no greater than about 1.75 mm). In some embodiments, OD5 of distal end 127 is at least about 0.9 mm (e.g., at least about 1 mm, at least about 1.1 mm, at least about 1.15 mm, at least about 1.2 mm). In some embodiments, OD5 is no greater than about 1.05 mm (e.g., no greater than about 1.2 mm, no greater than about 1.3 mm, no greater than about 1.4 mm). In an exemplary embodiment, OD4 is about 1.4 mm and OD5 is about 1.2 mm.

The inner diameter of tube 62 is constant along at least a portion (e.g., most or all) of its length.

Transition region 59 of tube 62 extends for at least a portion (e.g., most or all) of the length of tube 62 between its proximal and distal ends 125, 127. In some embodiments, transition region 59 is at least about 10% (e.g., at least about 25%, at least about 50%, at least about 75%) as long as the length of tube 62. In some embodiments, transition region 59 is no greater than about 15% (e.g., no greater than about 30%, no greater than about 45%, no greater than about 60%) of the length of tube 62.

A bumper 73 is secured (e.g., adhesively and/or mechanically such as by swaging) about inner member 12 proximal to stent 32. When outer member 14 is moved proximally to deploy stent 32, friction between inner layer 25 of the outer member and the stent can urge the stent proximally. Bumper 73 resists proximal movement of the stent and enhances accurate deployment. Bumper 73 can include or be formed of a radiopaque material (e.g., a metal or a doped polymer) to assist visualization of system 10 in use.

A distal tip 67 is secured about distal end 21 of distal tube portion 65 to assist navigation of the delivery system through body lumen 24.

As discussed above, outer layer 21 of outer member 14 can be formed of polymeric materials. Other components of outer member 14 and inner member 12 can also be formed of polymeric materials. Examples of polymeric materials from which any portion of system 10 (e.g., any portion of outer member 14 and/or inner member 12) can be formed include polyether-block co-polyamide polymers (e.g., PEBAX®), copolyester elastomers (e.g., Arnitel® copolyester elastomers), thermoplastic polyester elastomers (e.g., Hytrel®), thermoplastic polyurethane elastomers (e.g., Pellethane™), polyolefins (e.g., Marlex® polyethylene, Marlex® polypropylene), HDPEs, low-density polyethylenes (LDPEs), polyamides (e.g., Vestamid®), polyetherether ketones (e.g., PEEK™), and combinations of these materials. Outer member 14 or inner member 12 may include an additive (e.g., a fluoropolymer, a silicone, an ultrahigh molecular weight polyethylene, an oil, or blends thereof) to assist in the movement of outer member 14 with respect to inner member 12 and stent 32.

Stent 32 is typically formed of a shape memory alloy. Examples of shape memory alloys include nitinol, silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc/ (Cu—Zn), copper-zinc-aluminum (Cu—Zn—Al), copper-zinc-tin (Cu—Zn—Sn), copper-zinc-xenon (Cu—Zn—Xe), iron beryllium (Fe3Be), iron platinum (Fe3Pt), indium-thallium (In—Tl), iron-manganese (Fe—Mn), nickel-titanium-vanadium (Ni—Ti—V), iron-nickel-titanium-cobalt (Fe—Ni—Ti—Co) and copper-tin (Cu—Sn). For yet additional shape memory alloys, see, for example, Schetsky, L. McDonald, "Shape Memory. Alloys", Encyclopedia of Chemical Technology (3rd ed.), John Wiley & Sons, 1982, vol. 20. pp. 726-736.

Figure 5:
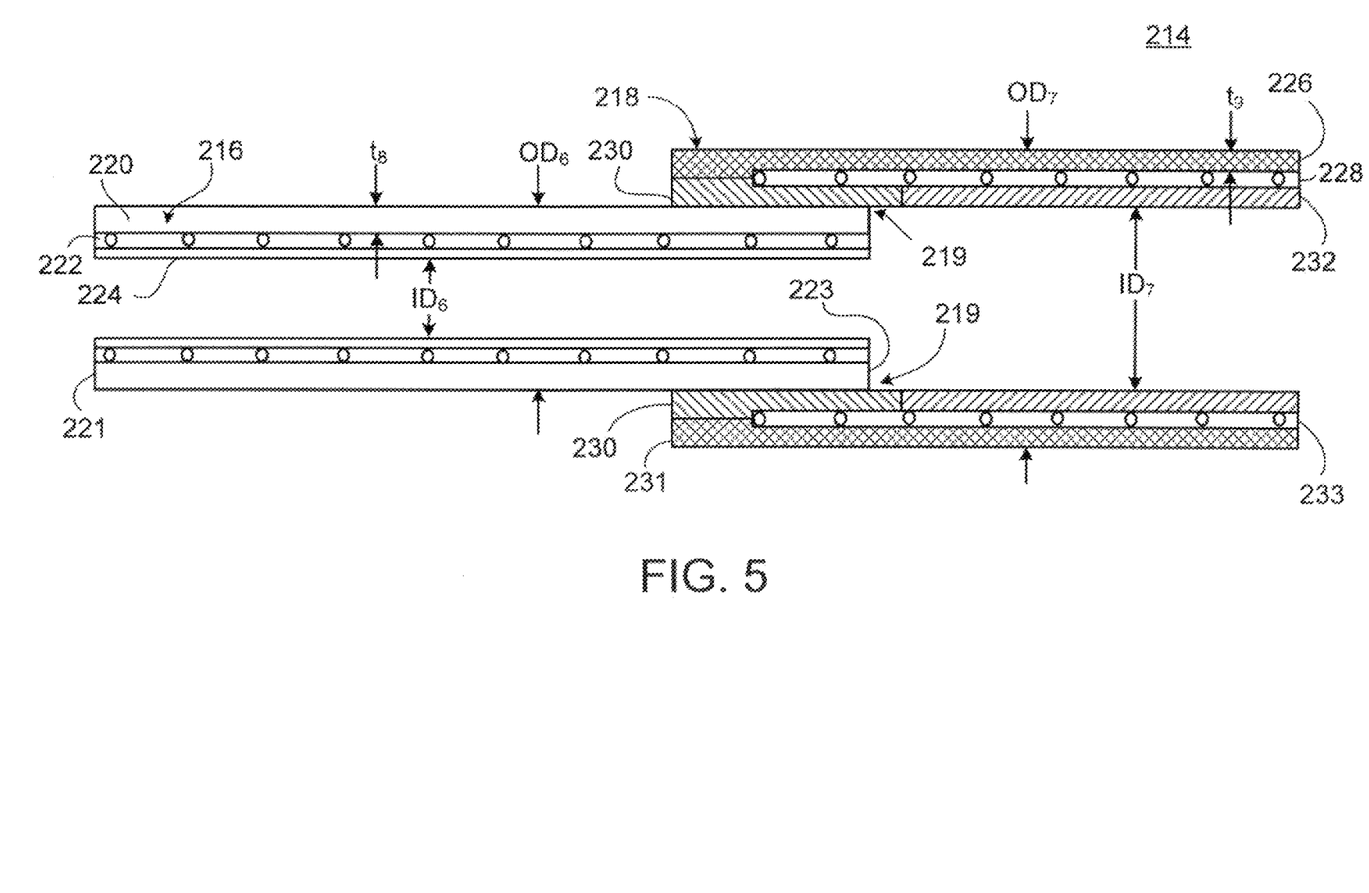
FIG. 5 is a cross-sectional side view of an embodiment of an outer member of an endoprosthesis delivery system.

Referring now to FIG. 5, an outer member 214 is discontinuous along its length having a proximal segment 216 and a distal segment 218 secured at a joint 219. Distal segment 218 is configured to accommodate a medical endoprosthesis (e.g., a stent) therein.

Proximal segment 216 extends between a proximal end 221 and a distal end 223. Proximal segment is multilayered having an outer layer 220, an intermediate layer 222, and an inner layer 224.

Proximal segment 216 defines an outer diameter OD6 along at least a portion (e.g., most or all) of its length. In general, outer diameter OD6 may be the same as outer diameter OD1 of outer member 14. In an exemplary embodiment, OD6 is about 1.73 mm.

Proximal segment 216 defines an inner diameter ID6 along at least a portion (e.g., all) of its length. In general, inner diameter ID6 may be the same as inner diameter ID1 of outer member 14. In an exemplary embodiment ID6 is about 1.37 mm.

Outer layer 220 of proximal segment 216 defines a thickness t8 along at least a portion (e.g., most or all) of its length. In general, outer layer 220 can have properties (e.g., dimensions and/or material) as described for proximal outer layer 33 of outer member 14. For example, thickness t8 may be the same as thickness t2 of outer layer 21 of outer member 14.

Inner layer 224 of proximal segment 216 can have properties (e.g., dimensions and/or material) as described for inner layer 25 of outer member 14. In general, inner layer 224 is formed of a lubricious material (e.g., PTFE).

Intermediate layer 222 is a reinforcing layer and can have (e.g., dimensions and/or material) as described for intermediate layer 23 of outer member 14.

Distal segment 218 extends between a proximal end 231 and a distal end 233. Distal segment is multilayered having an outer layer 226, an intermediate layer 228, a proximal inner layer 230, and a distal inner layer 232.

Distal segment 218 defines an outer diameter OD7 along at least a portion (e.g., all) of its length. Outer diameter OD7 is larger than OD6 of proximal segment 216. In general, OD7 can be the same as outer diameter OD3 of outer member 14. In an exemplary embodiment, OD7 is about 2.01 mm.

Distal segment 218 defines an inner diameter ID7 along at least a portion (e.g., all) of its length. Inner diameter ID7 is larger than ID6 of proximal segment 216. In general, inner diameter ID7 can be the same as inner diameter ID3 of outer member 14. In an exemplary embodiment ID6 is about 1.78 mm.

Outer layer 226 of distal segment 218 defines a thickness t9 along at least a portion (e.g., all) of its length. In general, outer layer 226 can have properties (e.g., dimensions and/or material) as described for distal outer layer 35 of outer member 14. For example, thickness t9 may be the same as thickness t4 of distal outer layer 35 of outer member 14. Alternatively, or in addition, the material from which outer layer 226 is formed can have a lower durometer than the material from which outer layer 220 is formed.

Distal inner layer 232 of distal segment 218 can be formed of the same material as inner layer 224.

Proximal inner layer 230 of distal segment 218 is generally formed of a material that can be secured (e.g., thermally and/or adhesively) to outer layer 220 of proximal segment 216. In some embodiments, the material from which proximal inner layer 230 is formed has a lower lubricity than the material from which distal inner layer 232 is formed. For example, in some embodiments, proximal inner layer 230 is formed of a polyamide (e.g., a nylon, such as Vestamid 2101) and distal outer layer 232 is formed of PTFE.

Intermediate layer 228 is a reinforcing layer and can have properties as described for intermediate layer 23 of outer member 14. In some embodiments, the proximal and distal intermediate layers 222, 228 are different. For example, in some embodiments, the distal intermediate layer 228 is a braid having relatively thin strands (e.g., ribbons) whereas the proximal intermediate layer 222 is a braid having thicker strands. The thinner strands of the distal intermediate layer minimize the thickness of the braid so that the inner diameter of the distal portion of outer member 214 is maximized with respect to the outer diameter of the distal portion. The thicker strands of the proximal intermediate layer provide enhanced resistance to elongation when the stent is deployed.

Outer member 214 and components thereof can be fabricated as desired. For example, fabrication of distal segment 218 typically includes positioning distal inner layer 232 (e.g., a PTFE tube) over a first portion of a mandrel having a first outer diameter. Proximal inner layer 230 (e.g., a nylon tube) is positioned over the exposed portion of the mandrel so that the inner layer 230 butts against the distal inner layer 232. Intermediate layer 228 (e.g., a flat braid) is drawn over the distal inner layer 232 so that an end of the braid is even with or extends just beyond the proximal end of the distal inner layer 232. Outer layer 226 (e.g., a PEBAX tube) is drawn over the braid and any exposed portion inner layer 230. The assembly is covered in heat shrink material, tacked with a heat source, and heated to about 215° C. for a time sufficient to secure the components.

Fabrication of proximal segment 216 typically includes positioning inner layer 224 (e.g., a PTFE tube) over a mandrel, which has a second outer diameter smaller than the first diameter of the mandrel used to form the distal segment. Intermediate layer 222 (e.g., a round braid) is drawn over the inner layer 224. Outer layer 220 (e.g., a nylon tube) is drawn over the braid. The assembly is covered in heat shrink and heated to secure the components.

Securing the proximal and distal segments typically includes positioning the proximal segment over a mandrel having the second diameter. The distal segment is placed over the same mandrel so that the proximal inner layer 230 of the distal segment overlaps a portion of outer layer 220 of the proximal segment. A hypotube is inserted between distal inner layer 232 and the mandrel to provide a smooth outer diameter transition wherein the proximal and distal segments are joined. The components are covered in heat shrink and heated to secure the proximal and distal segments.

While certain embodiments have been described, other embodiments are possible.

As an example, while systems including an outer member that has different proximal and distal outer layers have been described, an outer member can have other configurations. For example, the outer member can include a single outer layer, which may have thickness variations as described for outer layer 21. Alternatively, an outer member can include more than 2 different outer layers along its length (e.g., 3 outer layers, 4 outer layers, or more).

While outer member 14 has been described as having a proximal outer layer and a distal outer layer each defining thickness variations, the outer layers can have other configurations. For example, most (e.g., all) of the thickness variations can occur within only one of the proximal or distal outer layers. In such embodiments, one of the proximal or distal outer layers might exhibit a substantially uniform thickness along most or all of its length.

While outer member 14 has been described as having an outer diameter that varies along at least a portion of its length, the outer member can have other configurations. For example, the outer diameter of an outer member can be constant along most (e.g., all) of its length.

As another example, while an outer member having a transition portion in which the thickness of the outer layer decreases continuously has been described, the transition portion may have other configurations. For example, the thickness of the outer layer can vary discontinuously (e.g., in one or more steps) along at least a portion of its length.

Similarly, the thickness of tube 62 can vary discontinuously (e.g., in or more steps) along at least a portion of its length.

While tube 62 has been described as extending along the entire length of outer member 14, other tube configurations can be used. For example, an inner member can have a solid pushrod that extends along a proximal portion of device 10. In such embodiments, solid pushrod can reduce the length of the tube of the inner member relative to embodiments in which the solid pushrod is not present.

While a transition portion of tube 62 has been described as extending to a distal end of the tube, other tube configurations can be used. For example, a tube of an inner member can have a transition portion that terminates proximal to the distal end of the tube. In some embodiments, the transition region of the outer member may surround most (e.g., all) of the transition region of the tube of the inner member.

While bumper 73 has been described as secured with respect to tube 62, other configurations can be used. For example, in some embodiments, bumper 73 has at least some freedom of movement (e.g., longitudinal movement) with respect to tube 62. Tube 62 typically includes a stop (e.g., a shoulder) to limit or prevent proximal movement of the bumper while allowing movement between the stop and the distal end of the tube. Bumpers with at least some freedom of movement with respect to a tube are described in U.S. patent application Ser. No. 11/093,448, filed Mar. 30, 2005, and incorporated herein by reference in its entirety.

As another example, while systems including a self-expanding stent have been described, other types of implantable medical endoprostheses can be used in the systems. For example, the implantable medical endoprosthesis can be a balloon-expandable implantable medical endoprostheses (e.g., a balloon-expandable stent). In such systems, inner member 12 typically includes an expandable balloon in the region around which the implantable medical endoprostheses is housed during delivery. Additional examples of implantable medical endoprostheses include stent-grafts and filters (e.g., arterial filters, venus filters).

Other embodiments are within the scope of the following claims.

What is claimed is:

1. An implantable medical endoprosthesis delivery system, comprising:
an outer member including an inner layer, an intermediate layer and an outer layer, wherein the outer member defines a distal end and a length, and wherein the outer layer has a first thickness at a first position proximal of the distal end, a second thickness smaller than the first thickness at a second position closer to the distal end than the first position, the outer layer having a gradual transition region between the first thickness and the second thickness, and a third thickness larger than the second thickness at a third position closer to the distal end than the second position;
an inner member at least partially surrounded by the outer member; and
wherein the outer member is slidable along the inner member;
wherein,
the distal end of the outer member is disposed distal to an implantable medical endoprosthesis disposed between a distal portion of the outer and inner members;
the second position of the outer layer extends proximal of a proximal end of the implantable medical endoprosthesis;

the inner layer of the outer member has a uniform thickness and extends along the length of the outer member;

the inner layer defines an inner diameter of the outer member at any position along the outer member; and the outer member defines a first inner diameter and a first outer diameter at the first position of the outer layer, the outer member further defining a second inner diameter and a second outer diameter at the second position of the outer layer, wherein the second inner diameter and the second outer diameter are greater than the first inner diameter and the first outer diameter such that the outer member is flared along the gradual transition region between the first position and the second position.

2. The implantable medical endoprosthesis delivery system of claim 1, wherein the first thickness is at least about 10% thicker than the second thickness.

3. The implantable medical endoprosthesis delivery system of claim 1, wherein the first thickness is at least about 135 microns and the second thickness is about 115 microns or less.

4. The implantable medical endoprosthesis delivery system of claim 1, wherein, a ratio of a difference between the second inner diameter and the first inner diameter to a difference between the second outer diameter and the first outer diameter is greater than 1.

5. The implantable medical endoprosthesis delivery system of claim 4, wherein the ratio is at least about 2.

6. The implantable medical endoprosthesis delivery system of claim 5, wherein the ratio is at least about 3.25.

7. The implantable medical endoprosthesis delivery system of claim 4, wherein the distal portion of the outer member adjacent to the third position of the outer layer surrounds the implantable medical endoprosthesis.

8. The implantable medical endoprosthesis delivery system of claim 1, wherein a thickness of the inner member decreases from a first thickness at a first position proximal of a distal end of the inner member to a second, smaller thickness at a second position closer to the distal end of the inner member.

9. The implantable medical endoprosthesis delivery system of claim 8, wherein an outer diameter defined by the inner member decreases from a first outer diameter at the first position of the inner member to a second outer diameter at the second position of the member position.

10. The implantable medical endoprosthesis delivery system of claim 1, wherein the inner layer is surrounded by the outer layer.

11. The implantable medical endoprosthesis delivery system of claim 10, wherein the intermediate layer is disposed between the outer and inner layers.

12. The implantable medical endoprosthesis delivery system of claim 11, wherein the intermediate layer is a braid.

13. The implantable medical endoprosthesis delivery system of claim 12, wherein the braid extends at least between the first and second positions of the outer member.

14. The implantable medical endoprosthesis delivery system of claim 10, wherein the outer layer includes a distal outer layer and a proximal outer layer different from the distal outer layer, substantially all of the proximal outer layer being disposed proximal to the second position of the outer layer.

15. The implantable medical endoprosthesis delivery system of claim 14, wherein the proximal outer layer is formed from a material having a higher durometer than a material from which the distal outer layer is formed.

16. The implantable medical endoprosthesis delivery system of claim 14, wherein at least a portion of the proximal outer layer defines a thickness that decreases from the first thickness to a fourth thickness intermediate the first and second thicknesses.

17. The implantable medical endoprosthesis delivery system of claim 1, wherein the implantable medical endoprosthesis is a self expanding stent.

18. An implantable medical endoprosthesis delivery system, comprising:

an outer member including an inner layer, an intermediate layer and an outer layer, wherein the outer member defines a distal end and a length, wherein the outer layer has a first thickness at a first position proximal of the distal end, a second thickness smaller than the first thickness at a second position closer to the distal end than the first position, the outer layer having a gradual transition region between the first thickness and the second thickness, and a third thickness larger than the second thickness at a third position closer to the distal end than the second position;

an inner member at least partially surrounded by the outer member, the inner member including a distal portion and an outer diameter, wherein the outer diameter decreases continuously along the distal portion; and a bumper disposed about the inner member at the second position, wherein the bumper is free to move along at least a portion of the inner member;

wherein:

the outer member is slidable along the inner member;

the second position of the outer layer is disposed at least about 70 mm proximal to the distal end of the outer member;

the outer and inner members are configured so that an implantable medical endoprosthesis can be at least partially disposed therebetween, wherein the second position of the outer layer extends proximal of a proximal end of the implantable medical endoprosthesis;

the inner layer of the outer member has a uniform thickness and extends along the length of the outer member;

the inner layer of the outer member defines an inner diameter of the outer member at any position along the outer member and the outer member defines a first inner diameter and a first outer diameter at the first position of the outer layer, the outer member further defining a second inner diameter and a second outer diameter at the second position of the outer layer, wherein the second inner diameter and the second outer diameter are greater than the first inner diameter and the first outer diameter such that the outer member is flared along the gradual transition region between the first position and the second position;

a maximum outer diameter of the bumper is less than a third inner diameter of the outer member defined at the third position.

19. The implantable medical endoprosthesis delivery system of claim 18, wherein the second position of the outer layer is disposed at least about 90 mm proximal to the distal end of the outer member.

20. The implantable medical endoprosthesis delivery system of claim 18, wherein the first thickness is at least about 10% thicker than the second thickness.

21. An implantable medical endoprosthesis delivery system, comprising:

a multi-layered outer member including an inner layer, an intermediate layer and an outer layer, wherein the outer member defines a distal end and a length, wherein the outer layer of material defines a first thickness at a first position of the outer layer proximal of the distal end, a second thickness at a second position of the outer layer closer to the distal end than the first position, the first thickness being different from the second thickness, the outer layer having a gradual transition region between the first thickness and the second thickness, and a third thickness larger than the second thickness at a third position of the outer layer closer to the distal end than the second position;

an inner member at least partially surrounded by the outer member, wherein an outer diameter of the inner member decreases continuously along a distal portion of the inner member, the inner member defining a first outer diameter at a position aligned with the first position of the outer member and a second, smaller outer diameter at a position aligned with the second position of the outer member wherein the outer member is slidable along the inner member; and an implantable medical endoprosthesis is at least partially disposed between a distal portion of the outer member and the distal portion of the inner member, wherein the second position of the outer layer extends proximal of a proximal end the implantable medical endoprosthesis;

the inner layer of the outer member has a uniform thickness and extends along the length of the outer member;

the inner layer of the outer member defining an inner diameter of the outer member at any position along the outer member;

wherein, the outer member defines a first inner diameter and a first outer diameter at the first position of the outer layer, the outer member further defining a second inner diameter and a second outer diameter at the second position of the outer layer, wherein the second inner diameter and the second outer diameter are greater than the first inner diameter and the first outer diameter such that the outer member is flared along the gradual transition region between the first position and the second position;

wherein the outer member further defines a third inner diameter at the third position, the third inner diameter being greater than the first inner diameter.

* * * * *